(12) United States Patent
Bauerfeind et al.

(10) Patent No.: US 10,729,576 B2
(45) Date of Patent: Aug. 4, 2020

(54) PAD

(71) Applicant: BAUERFEIND AG, Zeulenroda-Triebes (DE)

(72) Inventors: Hans B. Bauerfeind, Zeulenroda-Triebes (DE); Rainer Scheuermann, Raisdorf (DE)

(73) Assignee: BAUERFEIND AG, Zeulenroda-Triebes (DE)

(*) Notice: Subject to any disclaimer, the term of this patent is extended or adjusted under 35 U.S.C. 154(b) by 342 days.

(21) Appl. No.: 15/534,581

(22) PCT Filed: Dec. 22, 2015

(86) PCT No.: PCT/EP2015/080987
§ 371 (c)(1),
(2) Date: Jun. 9, 2017

(87) PCT Pub. No.: WO2016/102574
PCT Pub. Date: Jun. 30, 2016

(65) Prior Publication Data
US 2017/0325990 A1    Nov. 16, 2017

(30) Foreign Application Priority Data
Dec. 22, 2014   (DE) ................. 10 2014 226 841

(51) Int. Cl.
*A61F 5/02*    (2006.01)
*A61F 5/30*    (2006.01)

(52) U.S. Cl.
CPC ............. *A61F 5/30* (2013.01); *A61F 5/028* (2013.01)

(58) Field of Classification Search
CPC .. A61F 5/30; A61F 5/028; A61F 5/024; A61F 5/026; A61F 5/05808; A61F 5/058; A61F 5/055; A61F 5/3707; A61F 5/37
See application file for complete search history.

(56) References Cited

U.S. PATENT DOCUMENTS

| 5,366,439 A * | 11/1994 | Peters ............. A43B 7/20 |
| | | 602/13 |
| 5,388,273 A | 2/1995 | Sydor et al. |
| 9,545,328 B2 | 1/2017 | Hess et al. |
| 2003/0171703 A1 | 9/2003 | Grim et al. |
| 2004/0138600 A1 | 7/2004 | Herzberg |
| 2011/0095142 A1 | 4/2011 | Quiroga et al. |

(Continued)

FOREIGN PATENT DOCUMENTS

| DE | 1469930 U | 4/1939 |
| DE | 867125 C | 2/1953 |

(Continued)

OTHER PUBLICATIONS

International Search Report for PCT/EP2015/080987, ISA/EP, Rijswijk, NL, dated Apr. 12, 2016.

(Continued)

*Primary Examiner* — Anna K Kinsaul
*Assistant Examiner* — Camtu T Nguyen
(74) *Attorney, Agent, or Firm* — Stephen T. Olson; Harness, Dickey & Pierce, P.L.C.

(57) ABSTRACT

A pad for a bandage or orthosis has a front surface and a rear surface. At least a subarea of the rear surface has connection pieces which form a mesh structure having interstices.

6 Claims, 5 Drawing Sheets

(56) References Cited

U.S. PATENT DOCUMENTS

2013/0338557 A1     12/2013   Hess et al.
2014/0005583 A1*    1/2014   Cardinali .................. A61F 5/01
                                                                                602/5

FOREIGN PATENT DOCUMENTS

| DE | 2722563 A1 | 11/1978 |
|----|------------|---------|
| DE | 29701001 U1 | 3/1997 |
| DE | 10103545 A1 | 8/2002 |
| DE | 102011010827 A1 | 8/2012 |
| DE | 202014100413 U1 | 2/2014 |
| EP | 1688107 A1 | 8/2006 |
| WO | WO-2012/069923 A1 | 5/2012 |

OTHER PUBLICATIONS

Written Opinion of the ISA for PCT/EP2015/080987, ISA/EP, Rijswijk, NL, dated Apr. 12, 2016.

English Translation of the International Preliminary Report on Patentability, IB, Geneva, dated Jun. 27, 2017, incorporating the English Translation of the Written Opinion of the ISA, dated Apr. 12, 2016.

* cited by examiner

PAD

CROSS-REFERENCE TO RELATED APPLICATIONS

This application is a 371 U.S. National Stage of International Application No. PCT/EP2015/080987, filed Dec. 22, 2015, which claims the benefit of and priority to German Application No. 10 2014 226 841.9, filed on Dec. 22, 2014. The disclosures of the above applications are incorporated herein by reference.

FIELD

The invention relates to pads for bandages and orthoses. The invention provides an improved pad that has a rear side having a mesh structure.

Pads are medical pressure pads for exerting and transferring pressure. They are used together with bandages or orthoses, for example in the back, hip, shoulder, arm or leg area.

Different pads are known, for example, from EP 1 688 107 A1, DE 101 03 545 A1, DE 27 22 56 3 A1 and DE 10 2011 010 827 A1.

Such pads can have a wide variety of three-dimensional shapes, for example, in the form of knobs, bulges or air channels, on the front side, that is, the side that faces the body of the person wearing the pad and is usually pressed against the person's skin. However, the rear side of the pads is usually smooth. Attachment elements in the form of snap fasteners, adhesive tapes or hook-and-loop fastener strips may be located on this smooth rear side to allow the pad to be attached to a bandage or orthosis. The basic shape of the pad, that is, the base of the pad, is a solid body that has a corresponding weight. The pads are made from a soft and flexible material, such as silicone rubber. Reinforcement elements are integrated into the pad base in pads that are intended to rigidly rest against the body of a wearer, for example in certain back pads used in the lower back area.

As a result, the pads from the prior art are heavy. It is also the case in pads from the prior art that the intensity of the effect of front projections, in particular knobs, can only be adjusted to an inadequate extent. Also, it is only possible to achieve the partially necessary stiffening of the pads using stabilization plates, in particular if the pads are to be inherently flexible and soft.

SUMMARY

The technical problem on which the invention is based is the provision of a pad, the weight of which can be reduced. It should also be possible to manufacture the pad in one piece. It should also be possible for the pads to optionally have areas having different flexibility or stiffness.

In particular, the invention solves the technical problem on which it is based using a pad for a bandage or orthosis, wherein the pad has a front surface and a rear surface, wherein at least a subarea of the rear surface has connection pieces that form a mesh structure having interstices.

Surprisingly, it was found that the formation of a mesh structure by connection pieces on the rear surface of a pad not only leads to a weight reduction, but thanks to the connection pieces and their specific design, for example, the width of the connection pieces and the shape and size of the interstices formed by the mesh structures, the stiffness of the pad can also be affected.

It was thus also found that the design and shape of the rear surface of the pad can influence the mode of operation and effective strength of the pad or certain areas of the pad.

In conjunction with the present invention, the front surface of a pad is understood to be the surface that faces the body when the pad is worn, in particular the surface that rests against the skin or clothes of the person using the pad or is pressed onto the skin or clothes of the person using the pad. In conjunction with the present invention, the rear surface of a pad is understood to be the surface opposite the front surface, that is, the surface that faces away from the body when the pad is being used. The rear surface can in particular face the inside of a bandage or orthosis and preferably be connected to the inside by means of connection elements.

The mesh structure can extend across a portion of the rear surface of the pad or across the entire rear surface of the pad. Preferably, the mesh structure extends over at least half of the rear surface of the pad. In a preferred embodiment, the mesh structure extends across the entire rear surface of the pad, in particular if the pad does not have any projections on the front surface.

Interstices are formed by the mesh structure that can have any shape and size. The number, shape and size of the interstices be changed to advantageously adjust the flexibility and softness or stiffness of the pad or also a certain subarea of the pad.

In a preferred embodiment, interstices are formed by the mesh structure that are polygonal, in particular square, rectangular, triangular, honeycomb shaped and diamond shaped, round or oval. The interstices are particularly preferably rectangular, honeycomb-shaped or triangular. With these shapes, the course of the connection pieces can have a particularly effective and simple design.

A preferred rectangular, in particular square, shape of the interstices results in a particularly simple and flexible embodiment. An alternative triangular shape of the interstices leads to an advantageous embodiment in which the transverse distortion of the pad is restricted to a greater extent. In a further alternative embodiment, the interstices can be diamond shaped such that this embodiment is particularly light.

Of course, different forms of interstices can also be combined. It can also be provided that individual subareas of the rear surface each have different forms of interstices.

The size of the interstices can be chosen as needed by those skilled in the art. The interstices preferably have a width and/or a height or diameter of at least 0.4 cm and at most 2 cm. The interstices particularly preferably have a height and/or width or diameter of at least 0.7 cm and at most 1.5 cm.

The depth of the interstices is equal to the height of the connection pieces. In conjunction with the present invention, the rear surface of the pad is formed by the outer surfaces formed by the connection pieces and not by the bottoms of the interstices. Thus, the interstices represent recesses in the rear surface.

The depth of the interstices can be freely chosen as needed by those skilled in the art. The depth of the interstices can, for example, make up about half of the total thickness of the pad, wherein the total thickness is equal to the distance of the front surface of the pad from the outer surfaces of the connection pieces.

The depth of the interstices is preferably at least 0.2 cm and at most 1 cm. The depth of the interstices is particularly preferably approximately 0.5.

Accordingly, the height of the connection pieces is also preferably 0.2 cm to 1 cm, particular preferably approximately 0.5 cm. The height of the connection pieces preferably corresponds to about half of the pad thickness.

The width of the connection pieces can also be chosen as needed by those skilled in the art. Preferably, the width of the connection pieces is at least 0.2 cm and at most 0.6 cm.

The length, width and height of the connection pieces can be changed to advantageously adjust the flexibility or stillness of the pad or the corresponding pad area.

The mesh structure according to the invention is formed by the intersection points of the connection pieces. For the purpose of stabilization, it can advantageously be provided that the connection pieces are widened at the intersection points.

The pad is preferably made of a permanently elastic material, in particular silicone rubber or polyurethane, preferably viscoelastic soft TPU. Foamed, soft materials, such as foamed, soft TPU can also be used. However, the invention is not limited to these materials. Those skilled in the art know of equally suitable materials. In particular, the physical-mechanical behavior of the material, especially the modulus of elasticity, is adapted to the intended use of the pad.

In a preferred embodiment, the pad is one piece and made of a single material. This enables simple and cost-effective production. Alternatively, it can also be provided that the pad has a stabilization plate, in particular that a stabilization plate is integrated into the pad body.

In a preferred embodiment, the pad according to the invention is a back pad or hip pad. Alternatively, the pad can also be a shoulder pad, arm pad, in particular an elbow pad, or a leg pad, in particular a pad for the knee area or the ankle area.

Because the pad according to the invention is for use together with a bandage or an orthosis, a pad is not understood to be an insole in conjunction with the present invention.

In a preferred embodiment, the front surface of the pad has projections.

In conjunction with the present invention, the projections are located on the front surface, which means the height of the projections is not included in the calculation for measuring the thickness of the pad.

The projections can have any shape, for example, they can be bead shaped, conical or knob shaped, in particular hemisphere shaped.

In a preferred embodiment, the projections are knob shaped, that is, knobs.

For example, the knobs can be friction knobs that cause a massage effect when the pad is worn due to pressure and friction.

In a preferred embodiment, the projections, in particular the knobs, are made of the same material as the pad. A single-piece pad thus also includes the projections, in particular knobs.

The projections, in particular knobs, of a pad are to exert particularly strong pressure at specific spots when the pad is worn. It is therefore advantageous if the pad is harder in the area of the projections, in particular knobs. However, in the areas in which there are no projections, in particular knobs, the pad should not be very hard, but should be rather soft because this makes it more comfortable to wear. The mesh structures according to the invention can be used advantageously for softer areas of the pad, while harder areas can be created for the knobs by omitting the mesh structure in those areas. This means that, in a preferred embodiment, the areas of the rear surface that are opposite the projections, in particular knobs, have no mesh structure, that is, no connection pieces having interstices are located there, but instead interstices there are filled with the pad base material. This makes it possible to realize a pad that is light and flexible in its basic structure thanks to the mesh structure, but is stiffer and harder in the area of the projections, in particular knobs. Thus, it is advantageously also possible to do without a stabilization plate on the inside of the pad and design the pad in one piece. The fact that there is no need for a stabilization plate in a pad according to the invention, in particular a back pad, the pad according to the invention can advantageously adapt to the anatomic surface of the body with which it comes into contact and even alternating pressure can be produced. However, if additionally required, a stabilization plate may be present.

The choice of whether or not the rear surface has a mesh structure in the area of individual projections, in particular knobs, makes it possible to advantageously determine whether the respective projection, in particular knob, presses more deeply or less deeply into the soft tissue of the body that comes into contact with the pad during use.

Thus, in a preferred embodiment, no interstices are formed in the areas of the rear surface that are opposite the areas of the front surface on which the projections, in particular knobs, are located. However, it can also be provided that no interstices are formed in only some of these areas of the rear surface that are opposite the areas of the front surface on which the projections, in particular knobs, are located.

On the rear surface, the pad can have attachment elements for attaching the pad to the inside of a bandage or orthosis. Such attachment elements can be, for example, snap fasteners, hook mechanisms, an adhesive tape or a hook-and-look fastener strip.

In a preferred embodiment, a back pad according to the invention has a total of seven to eleven knobs, preferably eight knobs, wherein the knobs form three horizontal rows, wherein the upper row has two to three, preferably two knobs, the middle row three to five, preferably four knobs, and the lower row has two to three, preferably two knobs.

The knobs preferably have a diameter between at least 1 cm and at most 2.5 cm, particularly preferably between at least 1.5 cm and at most 2 cm. The knobs arranged in a row preferably have a distance of at least 3 cm and at most 9 cm. The knobs preferably have a distance from the adjacent knobs of at least 3 cm and at most 9 cm.

The present invention also relates to a bandage or orthosis containing a pad according to the invention.

In a preferred embodiment, the bandage or orthosis is a back bandage or back orthosis. These bandages or orthoses can be designed as knitted orthoses or knitted bandages having an inserted pad according to the invention. Alternatively, it can also be a different bandage or orthosis, in particular a foot bandage, foot orthosis, knee bandage, knee orthosis, thigh bandage, thigh orthosis, hip bandage, hip orthosis, shoulder bandage, shoulder orthosis, elbow bandage, elbow orthosis and hand bandage or hand orthosis.

In a bandage or orthosis according to the invention, the pad according to the invention is preferably attached to the inside of the bandage or orthosis with the rear surface, in particular via at least one attachment element. Positioning and attachment options are known to those skilled in the art.

The subject matter of the invention is also the therapeutic and/or prophylactic use of the pad according to the invention in the treatment of lumbar spine syndrome by means of a pressure massage. In particular, the pad can be used for trigger point massages, friction massages, alternating pressure massages, intermittent compression, tension relief and/or skin surface stimulation.

The invention will be described in more detail on the basis of the figures below, without the embodiments of the invention shown there being understood as limiting.

DESCRIPTION OF EXEMPLARY EMBODIMENTS

Figure 1:
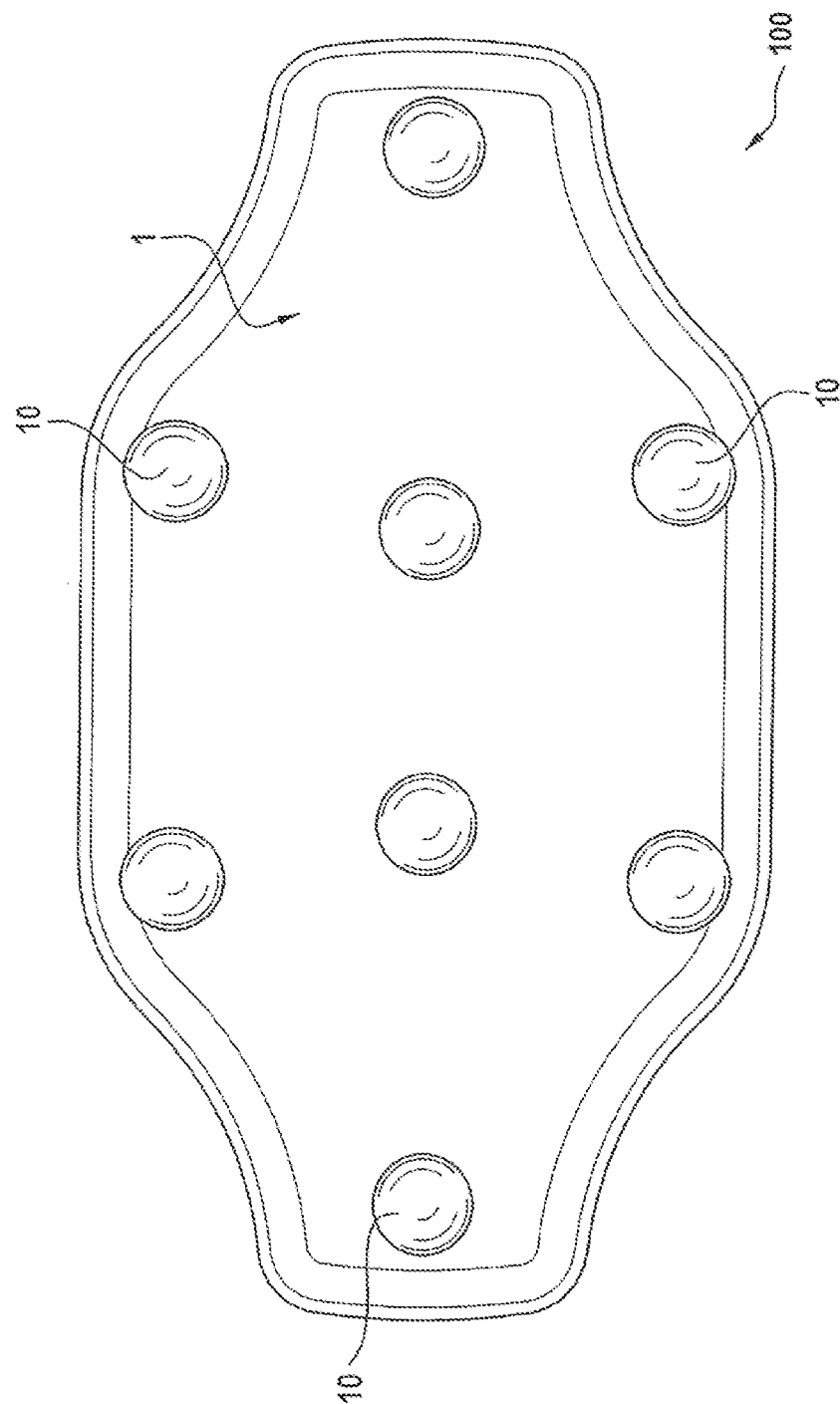
FIG. 1 shows the front surface of a preferred embodiment of the pad according to the invention.

FIG. 1 shows front surface 1 of a pad 100 according to the invention. Here, pad 100 is a back pad. Pad 100 is produced in one piece from a soft and flexible material. Surface 1 is rounded at the edges. Hemispherical friction knobs 10 are located on surface 1. The number and positioning of these advantageously results in the stimulation of trigger points by means of a friction massage in the back area.

Figure 2:
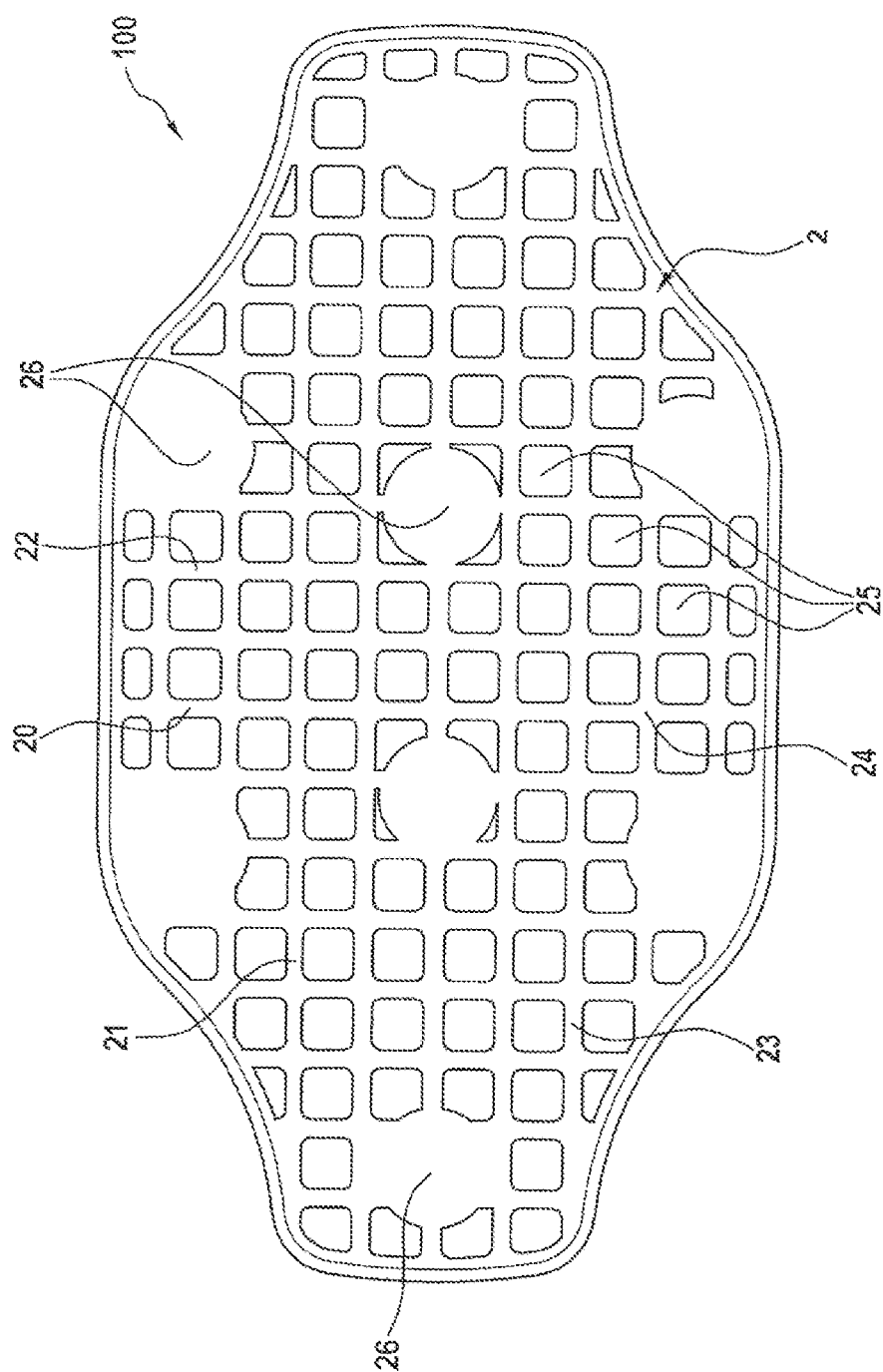
FIG. 2 shows a preferred embodiment of the rear surface of a pad according to the invention.

FIG. 2 shows rear surface 2 of back pad 100. Surface 2 is formed by the outer surfaces of a plurality of connection pieces 20, 21, 22, 23, which form a mesh structure having interstices 25 by means of intersection points 24. Thus, interstices 25 are recesses in rear surface 2. In the area of intersection points 24, the connection pieces 20, 21, 22, 23 are reinforced somewhat for stabilization. In the area of rear surface 2, on the opposite side of which there are knobs 10 on front surface 1 of pad 100, there is no mesh structure having interstices. Instead, the interstices are filled to the height of connection pieces 20, 21, 22, 23 and thus form hard areas 26, as a result of which the knobs are pressed onto the skin particularly well and particularly firmly through the bandage or orthosis when the pad is used with a bandage or orthosis.

In the embodiment shown, connection pieces 20, 21, 22. 23 form square recesses 25, wherein the corners of the recesses 25 are rounded by the thickened intersection points 24.

Figure 3:
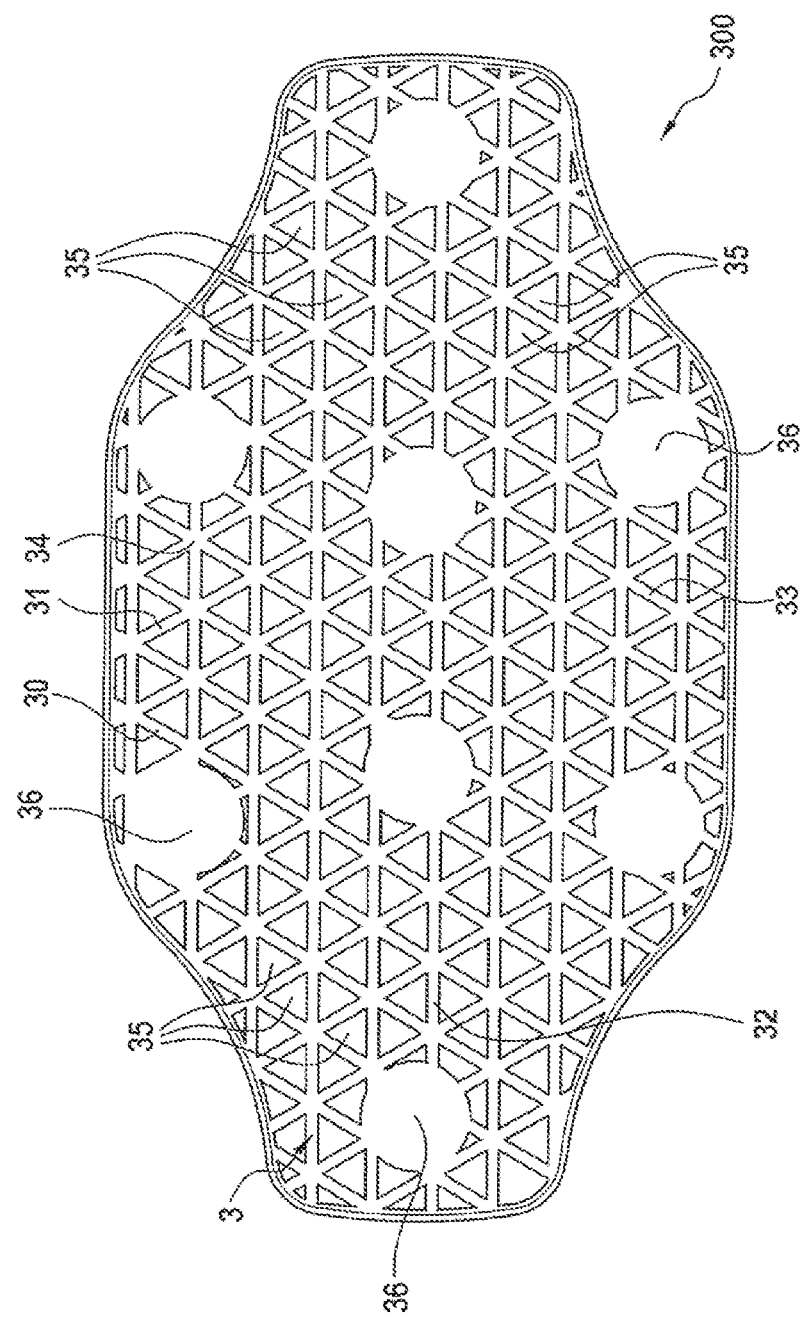
FIG. 3 shows an alternative embodiment of the rear surface of a pad according to the invention.

FIG. 3 shows an alternative embodiment of a rear surface 3 of a pad 300 according to the invention. This embodiment also has a plurality of connection pieces 30, 31, 32, 33, which form a mesh structure having interstices 35 by means of intersection points 34. There are also reinforcement points 36 in the area of the opposite knobs.

Compared to the square mesh structure of the embodiment of FIG. 2, the connection pieces 30, 31, 32, 33 shown here form a mesh structure having triangular interstices 35.

Because of this structure, the transverse distortion of pad 300 is restricted to a greater extent.

Figure 4:
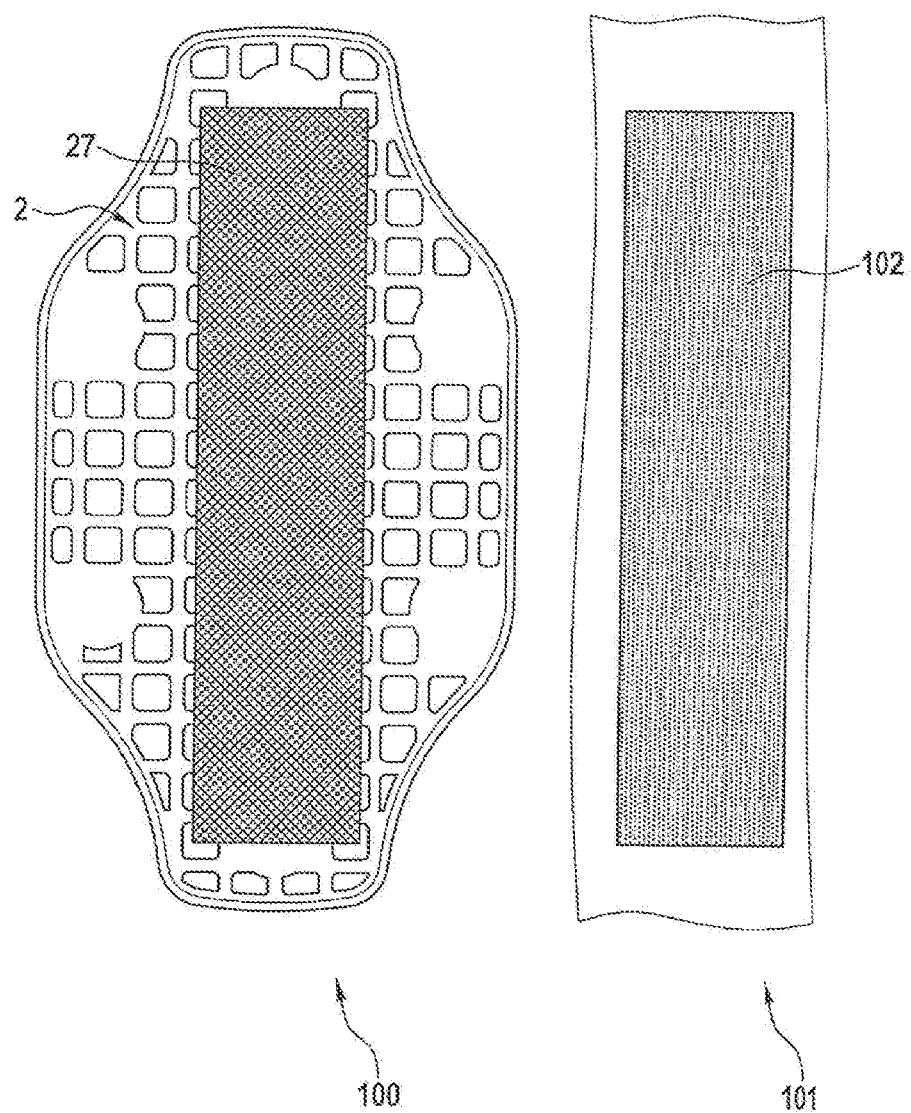
FIG. 4 shows a pad according to the invention together with a bandage.

FIG. 4 shows a pad 100 according to the invention together with a part of a bandage 101. Rear surface 2 of pad 100 has a hook-and-loop fastener strip 27 with which pad 100 can be attached to a fleece strip 102 of bandage 101.

Figure 5:
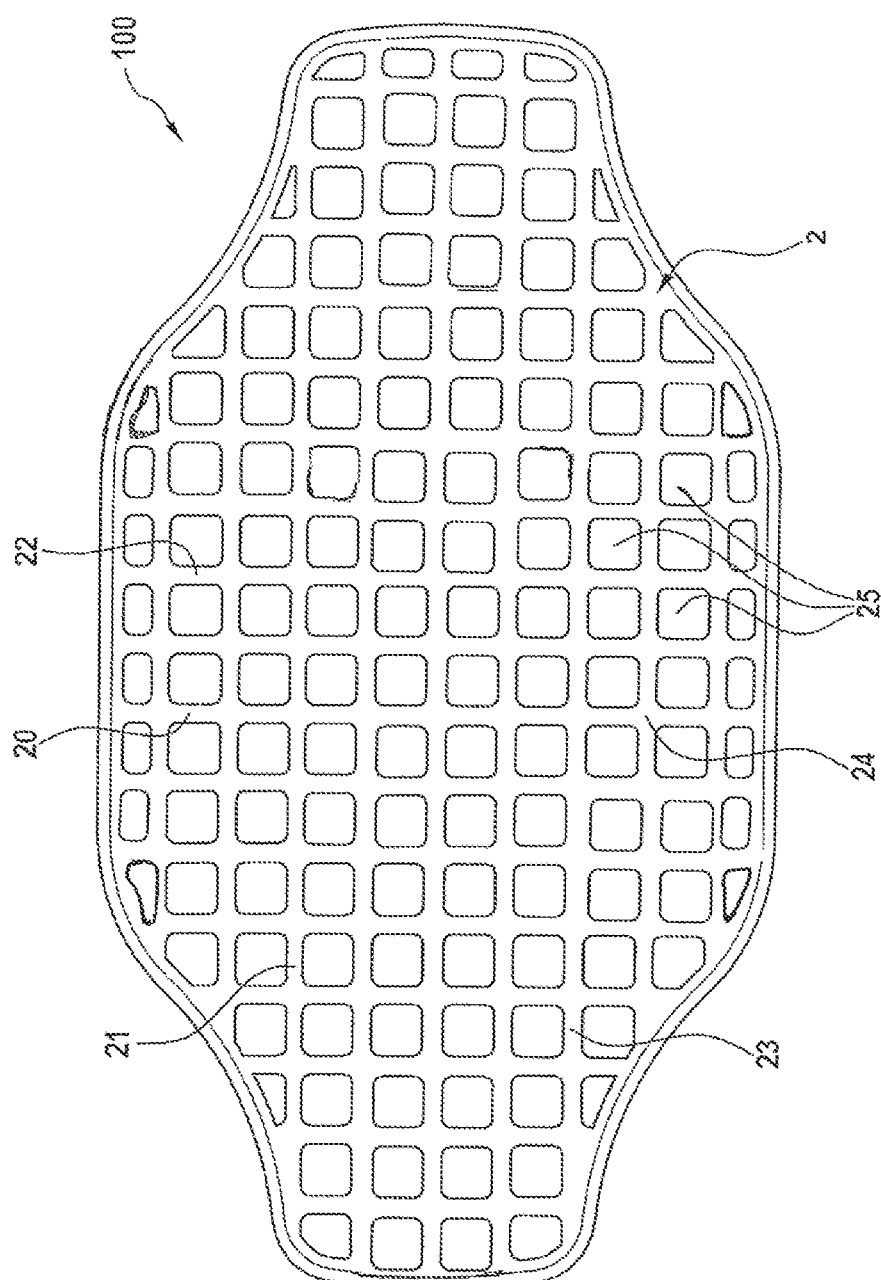
FIG. 5 shows a further alternative embodiment of the rear surface of a pad according to the invention.

FIG. 5 shows a further alternative embodiment of rear surface 2 of a pad 100 according to the invention. The design is fundamentally the same as in FIG. 2. In the embodiment shown, connection pieces 20, 21, 22, 23 again form square recesses 25, wherein the corners of the recesses 25 are rounded by the thickened intersection points 24. However, in the area of rear surface 2, on the opposite side of which there are knobs 10 on front surface 1 of pad 100, there is no mesh structure having interstices here either. Thus, there are no hard areas here. This results in a softer pad than the one from FIG. 2.

The invention claimed is:

1. A back pad for a bandage or orthosis, the back pad comprising:
    a front surface having a plurality of projections; and
    a rear surface, at least a subarea of the rear surface having connection pieces forming a mesh structure with interstices, the rear surface including opposed areas that are directly opposite each projection of the plurality of projections on the front surface;
    wherein the back pad is made in one piece and from a single material, and
    wherein no interstices are formed in the opposed areas of the rear surface.

2. The back pad according to claim 1, wherein the interstices formed by the mesh structure are rectangular, triangular, honeycomb shaped, diamond shaped, round or oval.

3. The back pad according to claim 1, wherein the mesh structure extends across an entirety of the rear surface of the back pad.

4. The back pad according to claim 1, wherein the projections are knob shaped.

5. The back pad of claim 1, wherein the opposed areas of the rear surface are hard areas of the rear surface.

6. A back pad for a bandage or orthosis, the back pad comprising:
    a front surface having a plurality of projections; and
    a rear surface including opposed areas that are directly opposite each projection of the plurality of projections on the front surface, the rear surface further including a mesh structure with a plurality of connection pieces, the connection pieces cooperating to define a plurality of interstices;
    wherein the opposed areas are continuous and formed without any interstices,
    wherein the connection pieces have a height and the interstices have a depth equal to the height of the connection pieces.

* * * * *